(12) United States Patent
Noguchi et al.

(10) Patent No.: US 12,398,361 B2
(45) Date of Patent: Aug. 26, 2025

(54) PROGRAM FOR OPERATING CELL CULTURE SUPPORT APPARATUS, CELL CULTURE SUPPORT APPARATUS, AND METHOD FOR OPERATING CELL CULTURE SUPPORT APPARATUS

(71) Applicant: FUJIFILM Corporation, Tokyo (JP)

(72) Inventors: Yukihisa Noguchi, Kanagawa (JP); Masataka Hasegawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 834 days.

(21) Appl. No.: 17/172,779

(22) Filed: Feb. 10, 2021

(65) Prior Publication Data

US 2021/0163874 A1 Jun. 3, 2021

Related U.S. Application Data

(63) Continuation of application No. PCT/JP2019/021822, filed on May 31, 2019.

(30) Foreign Application Priority Data

Aug. 22, 2018 (JP) .................................. 2018-155748

(51) Int. Cl.
| | | |
|---|---|---|
| C12M 1/36 | (2006.01) | |
| C12M 1/34 | (2006.01) | |
| G16B 40/00 | (2019.01) | |

(52) U.S. Cl.
CPC ............ C12M 41/48 (2013.01); C12M 41/46 (2013.01); G16B 40/00 (2019.02)

(58) Field of Classification Search
CPC ....... C12M 41/48; C12M 41/46; G16B 40/00; G06N 3/084
(Continued)

(56) References Cited

U.S. PATENT DOCUMENTS

2018/0320127 A1* 11/2018 Cannon ................ G16B 50/00
2021/0292704 A1* 9/2021 Cannon ................ C12M 41/12

FOREIGN PATENT DOCUMENTS

| EP | 1 816 188 A1 | 8/2007 |
|---|---|---|
| JP | 2009-44974 A | 3/2009 |

(Continued)

OTHER PUBLICATIONS

Li, F. et al. (2010). "Cell culture processes for monoclonal antibody production." Mabs. 2(5). 466-79. (Year: 2010).*

(Continued)

Primary Examiner — Jill A Warden
Assistant Examiner — Jacqueline Brazin
(74) Attorney, Agent, or Firm — Birch, Stewart, Kolasch & Birch, LLP

(57) ABSTRACT

A program for operating a cell culture support apparatus causes a computer to function as a first acquisition unit, a second acquisition unit, and a first derivation unit. The first acquisition unit acquires a learned model indicating a relationship between an initial culture process and a production culture process, derived by performing machine learning on the basis of initial record data for learning including a set of culture condition data indicating a record of culture conditions and culture result data indicating a record of culture results in the initial culture process, and production record data for learning, corresponding to the initial record data for learning and including a set of culture condition data indicating a record of culture conditions and culture result data indicating a record of culture results in the production culture process. The second acquisition unit acquires initial record data for analysis including a set of the culture condition data indicating the record of the culture conditions and the culture result data indicating the record of the culture results in the initial culture process, and temporary culture condition data indicating temporary culture conditions in the production culture process. The first derivation unit derives predicted culture result data obtained by predicting the culture result data in the production culture process, from the learned model acquired in the first acquisition unit, and the initial record data for analysis and the temporary culture condition data acquired in the second acquisition unit.

6 Claims, 15 Drawing Sheets

(58) Field of Classification Search
USPC .................................................... 435/287.2
See application file for complete search history.

(56) References Cited

FOREIGN PATENT DOCUMENTS

| | | |
|---|---|---|
| WO | WO 2011/021391 A1 | 2/2011 |
| WO | WO 2018/142702 A1 | 8/2018 |

OTHER PUBLICATIONS

Li, F., et al. (2010). "Cell culture processes for monoclonal antibody production." mAbs. 2:5. 466-477. (Year: 2010).*
International Preliminary Report on Patentability and Written Opinion of the International Searching Authority (Forms PCT/IB/326, PCT/IB/373 and PCT/ISA/237) for corresponding International Application No. PCT/JP2019/021822, dated Mar. 4, 2021, with an English translation.
International Search Report (Form PCT/ISA/210) for corresponding International Application No. PCT/JP2019/021822, dated Aug. 27, 2019, with English translation.
Extended European Search Report for corresponding European Application No. 19851034.9, dated Aug. 9, 2021.
Wysotzki, "Machine Learning and its Application to Process Control," Operations Research '91, 1991, 2 pages total.

* cited by examiner

FIG. 10

| CULTURE ID | INITIAL RECORD DATA | | PRODUCTION RECORD DATA | |
|---|---|---|---|---|
| | CULTURE CONDITION DATA | CULTURE RESULT DATA | CULTURE CONDITION DATA | CULTURE RESULT DATA |
| 001 | X1α_001 | X2α_001 | X3α_001 | Yα_001 |
| 002 | X1α_002 | X2α_002 | X3α_002 | Yα_002 |
| 003 | X1α_003 | X2α_003 | X3α_003 | Yα_003 |
| 004 | X1α_004 | X2α_004 | X3α_004 | Yα_004 |

TRAINING DATA (MEDICINE α)
TRAINING DATA (MEDICINE β)
TRAINING DATA (MEDICINE γ)

CELL CULTURE SUPPORT APPLICATION          ~INPUT SCREEN~

- PLEASE INPUT CULTURE PURPOSE.

CULTURE PURPOSE: MEDICINE α

- PLEASE INPUT CULTURE CONDITION DATA IN INITIAL CULTURE PROCESS.

[REFERENCE]

- PLEASE INPUT CULTURE RESULT DATA IN INITIAL CULTURE PROCESS.

[REFERENCE]

- PLEASE INPUT TEMPORARY CULTURE CONDITION DATA IN PRODUCTION CULTURE PROCESS.

[DATA SET]

[OK]

PROGRAM FOR OPERATING CELL CULTURE SUPPORT APPARATUS, CELL CULTURE SUPPORT APPARATUS, AND METHOD FOR OPERATING CELL CULTURE SUPPORT APPARATUS

CROSS-REFERENCE TO RELATED APPLICATIONS

This application is a continuation application of International Application No. PCT/JP2019/021822 filed May 31, 2019, the disclosure of which is incorporated herein by reference in its entirety. Further, this application claims priority from Japanese Patent Application No. 2018-155748 filed on Aug. 22, 2018, the disclosure of which is incorporated herein by reference in its entirety.

BACKGROUND OF THE INVENTION

1. Technical Field

The present disclosure relates to a program for operating a cell culture support apparatus, the cell culture support apparatus, and a method for operating the cell culture support apparatus.

2. Description of the Related Art

Cell culture for culturing cells collected from a living body has been actively performed. JP2009-044974A discloses a technique for performing a fuzzy neural network analysis on the basis of a set of indicators related to cell morphology such as a cell area and a circumference length and measured data related to cell quality such as a cell proliferation rate and the degree of differentiation, and predicting cell quality from the indicators related to the cell morphology.

SUMMARY

Cell culture requires a relatively long period of about 40 weeks. This is because, as conceptually shown in FIG. 19, an intermediate culture process, which requires many experiments, should be performed from a relatively small initial culture process using a petri dish or a flask having a capacity of several to several tens of milliliters to a relatively large production culture process using a tank with a capacity of several hundred to several thousand liters. For example, in the intermediate culture process, it is necessary to repeat an experiment for optimizing various parameters such as the amount of components to be added daily to a medium, a stirring rate, and an environment temperature/humidity by using cells into which an antibody gene has been introduced and a medium, selected in the initial culture process. FIG. 19 shows a state where setting of culture conditions, culture, and evaluation are repeated until an evaluation result is OK in an initial culture process and three intermediate culture processes (intermediate culture processes 1 to 3).

The technique described in JP2009-044974A is configured to predict the cell quality from the indicators related to the cell morphology in one culture process such as an initial culture process. Therefore, the technique contributes to shortening one culture process, but its effect is limiting.

An object of the present disclosure is to provide a program for operating a cell culture support apparatus, the cell culture support apparatus, and a method for operating the cell culture support apparatus capable of significantly shortening a period from an initial culture process to a production culture process, in cell culture.

In order to achieve the above object, according to an aspect of the present disclosure, there is provided a program for operating a cell culture support apparatus for supporting cell culture from an initial culture process to a production culture process performed in a facility larger than the initial culture process, the program causing a computer to function as: a first acquisition unit that acquires a learned model indicating a relationship between the initial culture process and the production culture process, derived by performing machine learning on the basis of initial record data for learning including a set of culture condition data indicating a record of culture conditions and culture result data indicating a record of culture results in the initial culture process, and production record data for learning, corresponding to the initial record data for learning and including a set of culture condition data indicating a record of culture conditions and culture result data indicating a record of culture results in the production culture process; a second acquisition unit that acquires initial record data for analysis including a set of the culture condition data indicating the record of the culture conditions and the culture result data indicating the record of the culture results in the initial culture process, and temporary culture condition data indicating temporary culture conditions in the production culture process; and a first derivation unit that derives predicted culture result data obtained by predicting the culture result data in the production culture process, from the learned model acquired in the first acquisition unit, and the initial record data for analysis and the temporary culture condition data acquired in the second acquisition unit.

It is preferable that the program causes the computer to function as a first output control unit that performs a control for outputting the predicted culture result data.

It is preferable that in a case where a plurality of pieces of the temporary culture condition data are acquired by the second acquisition unit, the first derivation unit derives the predicted culture result data for each of the plurality of pieces of the temporary culture condition data, and selects the best temporary culture condition data having the best predicted culture result data among the plurality of pieces of the temporary culture condition data.

It is preferable that the program causes the computer to function as a second output control unit that performs a control for outputting the best temporary culture condition data.

It is preferable that the program causes the computer to function as a third acquisition unit that acquires the initial record data for learning and the production record data for learning, and a second derivation unit that derives the learned model by performing the machine learning on the basis of the initial record data for learning and the production record data for learning acquired in the third acquisition unit.

It is preferable that the initial culture process is a process of selecting cells into which an antibody gene has been introduced and a medium, and the production culture process is a process of producing an antibody-based medicine.

According to another aspect of the present disclosure, there is provided a cell culture support apparatus for supporting cell culture from an initial culture process to a production culture process performed in a facility larger than the initial culture process, the apparatus comprising: a first acquisition unit that acquires a learned model indicating a relationship between the initial culture process and the production culture process, derived by performing machine learning on the basis of initial record data for learning including a set of culture condition data indicating a record of culture conditions and culture result data indicating a record of culture results in the initial culture process, and production record data for learning, corresponding to the initial record data for learning and including a set of culture condition data indicating a record of culture conditions and culture result data indicating a record of culture results in the production culture process; a second acquisition unit that acquires initial record data for analysis including a set of the culture condition data indicating the record of the culture conditions and the culture result data indicating the record of the culture results in the initial culture process, and temporary culture condition data indicating temporary culture conditions in the production culture process; and a first derivation unit that derives predicted culture result data obtained by predicting the culture result data in the production culture process, from the learned model acquired in the first acquisition unit, and the initial record data for analysis and the temporary culture condition data acquired in the second acquisition unit.

According to still another aspect of the present disclosure, there is provided a method for operating a cell culture support apparatus for supporting cell culture from an initial culture process to a production culture process performed in a facility larger than the initial culture process, the method comprising: a first acquisition step of acquiring a learned model indicating a relationship between the initial culture process and the production culture process, derived by performing machine learning on the basis of initial record data for learning including a set of culture condition data indicating a record of culture conditions and culture result data indicating a record of culture results in the initial culture process, and production record data for learning, corresponding to the initial record data for learning and including a set of culture condition data indicating a record of culture conditions and culture result data indicating a record of culture results in the production culture process; a second acquisition step of acquiring initial record data for analysis including a set of the culture condition data indicating the record of the culture conditions and the culture result data indicating the record of the culture results in the initial culture process, and temporary culture condition data indicating temporary culture conditions in the production culture process; and a first derivation step of deriving predicted culture result data obtained by predicting the culture result data in the production culture process, from the learned model acquired in the first acquisition step, and the initial record data for analysis and the temporary culture condition data acquired in the second acquisition step.

Further, according to still another aspect of the present disclosure, there is provided a cell culture support apparatus for supporting cell culture from an initial culture process to a production culture process performed in a facility larger than the initial culture process, the apparatus comprising: a first acquisition processor that acquires a learned model indicating a relationship between the initial culture process and the production culture process, derived by performing machine learning on the basis of initial record data for learning including a set of culture condition data indicating a record of culture conditions and culture result data indicating a record of culture results in the initial culture process, and production record data for learning, corresponding to the initial record data for learning and including a set of culture condition data indicating a record of culture conditions and culture result data indicating a record of culture results in the production culture process; a second acquisition processor that acquires initial record data for analysis including a set of the culture condition data indicating the record of the culture conditions and the culture result data indicating the record of the culture results in the initial culture process, and temporary culture condition data indicating temporary culture conditions in the production culture process; and a first derivation processor that derives predicted culture result data obtained by predicting the culture result data in the production culture process, from the learned model acquired in the first acquisition processor, and the initial record data for analysis and the temporary culture condition data acquired in the second acquisition processor.

According to the present disclosure, it is possible to provide a program for operating a cell culture support apparatus, the cell culture support apparatus, and a method for operating the cell culture support apparatus capable of significantly shortening a period from the initial culture process to the production culture process, in cell culture.

BRIEF DESCRIPTION OF THE DRAWINGS

Exemplary embodiments according to the technique of the present disclosure will be described in detail based on the following figures, wherein:

FIG. 10 is a diagram showing content of training data;

FIG. 11 is a diagram showing an input screen of a culture purpose, culture condition data and culture result data of an initial culture process, and temporary culture condition data of a production culture process;

DETAILED DESCRIPTION

Figure 1:
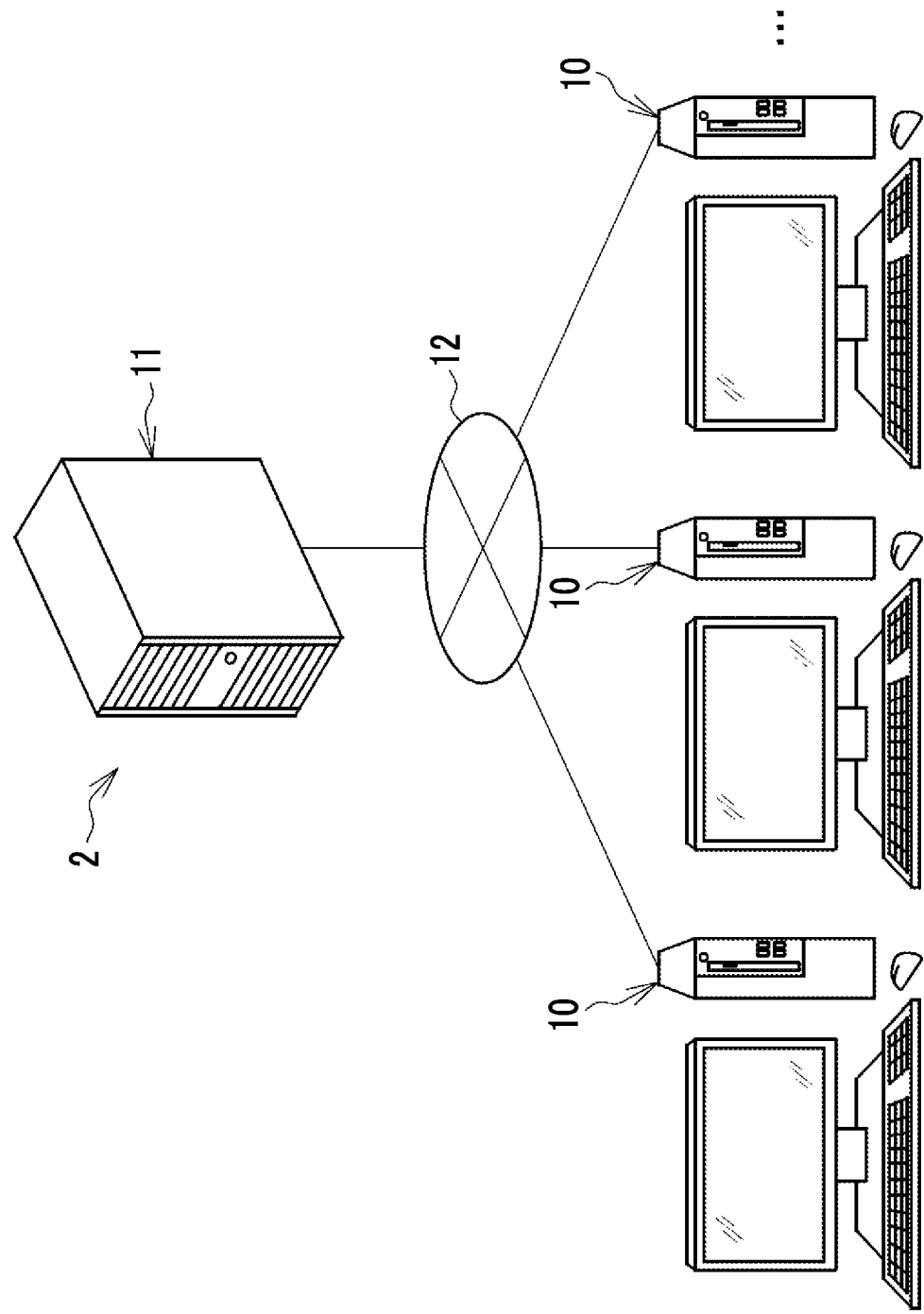
FIG. 1 is a diagram showing a cell culture system.

In FIG. 1, a cell culture system 2 comprises an operator terminal 10 and a cell culture support server 11, and is installed in one cell culture laboratory, for example. The operator terminal 10 is a terminal operated by an operator of cell culture, and is configured by a desktop personal computer, for example. The cell culture support server 11 corresponds to a cell culture support apparatus, and is configured by a server computer. The operator terminal 10 and the cell culture support server 11 are connected to each other through a network 12 such as a local area network (LAN) to communicate with each other.

The operator terminal 10 and the cell culture support server 11 are based on a computer such as a personal computer, a server computer, or a workstation. The operator terminal 10 and the cell culture support server 11 are configured by installing a control program such as an operating system and various application programs on such a computer.

Figure 2:
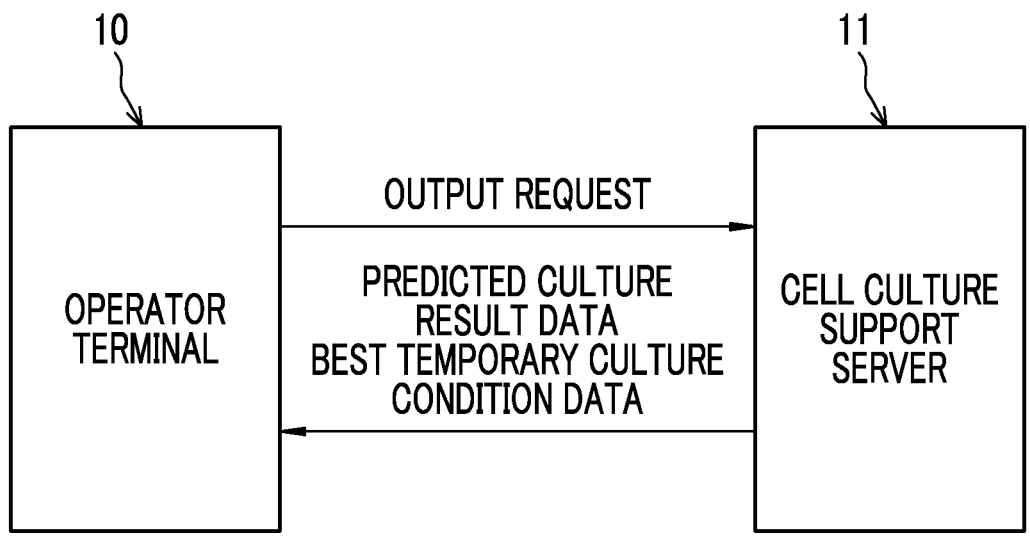
FIG. 2 is a diagram showing a request transmitted from an operator terminal to a cell culture support server and information transmitted from the cell culture support server to the operator terminal.

In FIG. 2, the operator terminal 10 transmits an output request for predicted culture result data or an output request of the best temporary culture condition data to the cell culture support server 11. The predicted culture result data is data obtained by predicting a culture result of cell culture in a production culture process of producing an antibody-based medicine in a relatively large-scale facility such as a tank having a capacity of several hundred to several thousand liters. The best temporary culture condition data is such data that the predicted culture result data is the best among a plurality of pieces of temporary culture condition data. The temporary culture condition data is data showing temporary culture conditions of cell culture in the production culture process.

The cell culture support server 11 receives the output request for the predicted culture result data, derives the predicted culture result data, and outputs the derived predicted culture result data to the operator terminal 10 that is an output request source. Further, the cell culture support server 11 receives the output request for the best temporary culture condition data, selects the best temporary culture condition data from the plurality of pieces of temporary culture condition data, and outputs the selected best temporary culture condition data to the operator terminal 10 that is the output request source. In the following description, unless it is necessary to distinguish between the predicted culture result data and the best temporary culture condition data, the predicted culture result data and the best temporary culture condition data are collectively referred to as guideline information.

The cell culture support server 11 generates a guideline information display screen 80 (see FIGS. 14 and 15) that is viewable on a web browser of the operator terminal 10 as one form of an output of the guideline information, and outputs the generated guideline information display screen 80 to the operator terminal 10. More specifically, the cell culture support server 11 outputs the guideline information display screen 80 in the form of screen data for web distribution created in a markup language such as Extensible Markup Language (XML). Instead of XML, another data description language such as JavaScript (registered trademark) Object Notation (JSON) may be used. In addition to the guideline information display screen 80, the cell culture support server 11 outputs various screens to the operator terminal 10 in the form of screen data for web distribution.

Figure 3:
FIG. 3 is a diagram showing a request transmitted from the operator terminal to the cell culture support server.

In FIG. 3, the operator terminal 10 further transmits a registration request for initial record data (see FIG. 4) and a registration request for production record data (see FIG. 5) to the cell culture support server 11. The cell culture support server 11 receives the registration request for the initial record data, and registers the initial record data. Further, the cell culture support server 11 receives the registration request for the production record data, and registers the production record data.

The output request for the guideline information includes the initial record data and the temporary culture condition data. Further, the registration request for the initial record data includes the initial record data, and the registration request of the production record data includes the production record data, respectively.

Figure 4:
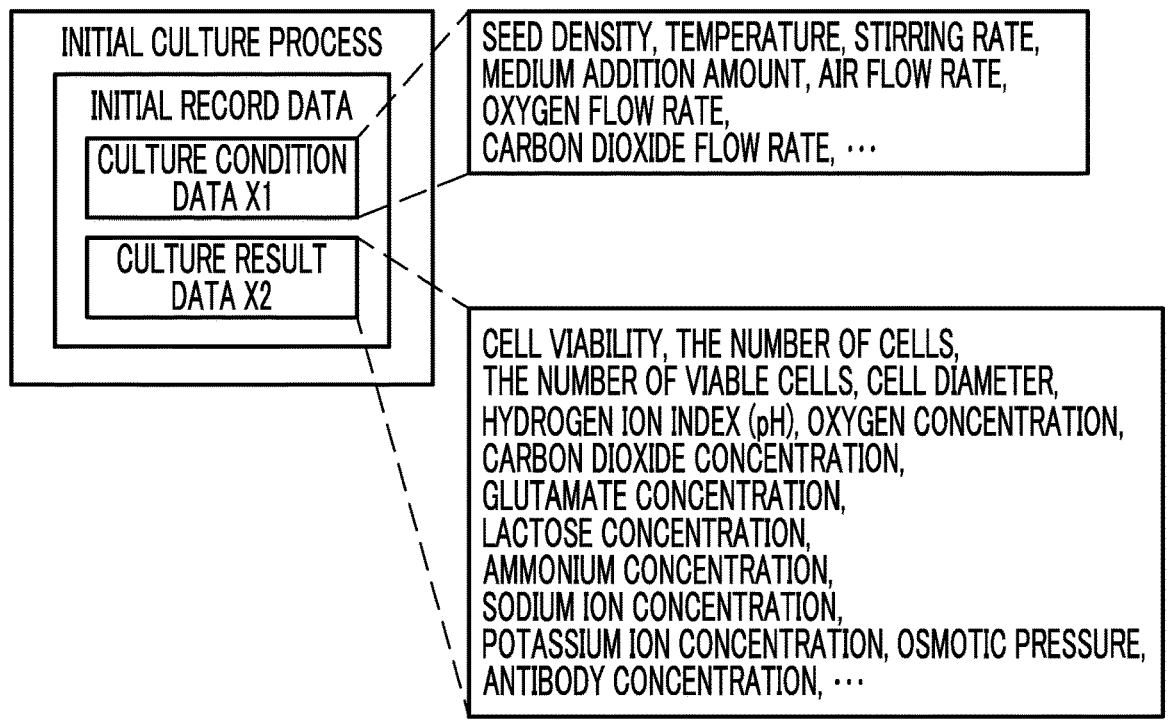
FIG. 4 is a diagram showing initial record data.

As shown in FIG. 4, the initial record data is a set of culture condition data X1 showing a record of culture conditions in the initial culture process and culture result data X2 showing a record of culture results obtained by performing cell culture with the culture condition data X1. Here, the initial culture process is performed prior to the production culture process, which is a process of selecting antibody gene introduced cells and a medium in a relatively small-scale facility such as a petri dish or a flask having a capacity of several to several tens of milliliters. The culture condition data X1 of the initial record data is a set of respective conditions of a plurality of processes performed in the initial culture process. Specifically, the culture condition data X1 of the initial record data includes a seed density, a temperature, a stirring rate, a medium addition amount, an air flow rate, an oxygen flow rate, a carbon dioxide flow rate, and the like. In addition, the culture result data X2 of the initial record data specifically includes a cell viability, the number of cells, the number of viable cells, a cell diameter, a hydrogen ion index (pH), an oxygen concentration, a carbon dioxide concentration, a glutamate concentration, and a lactose concentration, an ammonium concentration, a sodium ion concentration, a potassium ion concentration, an osmotic pressure, an antibody concentration, and the like.

Figure 5:
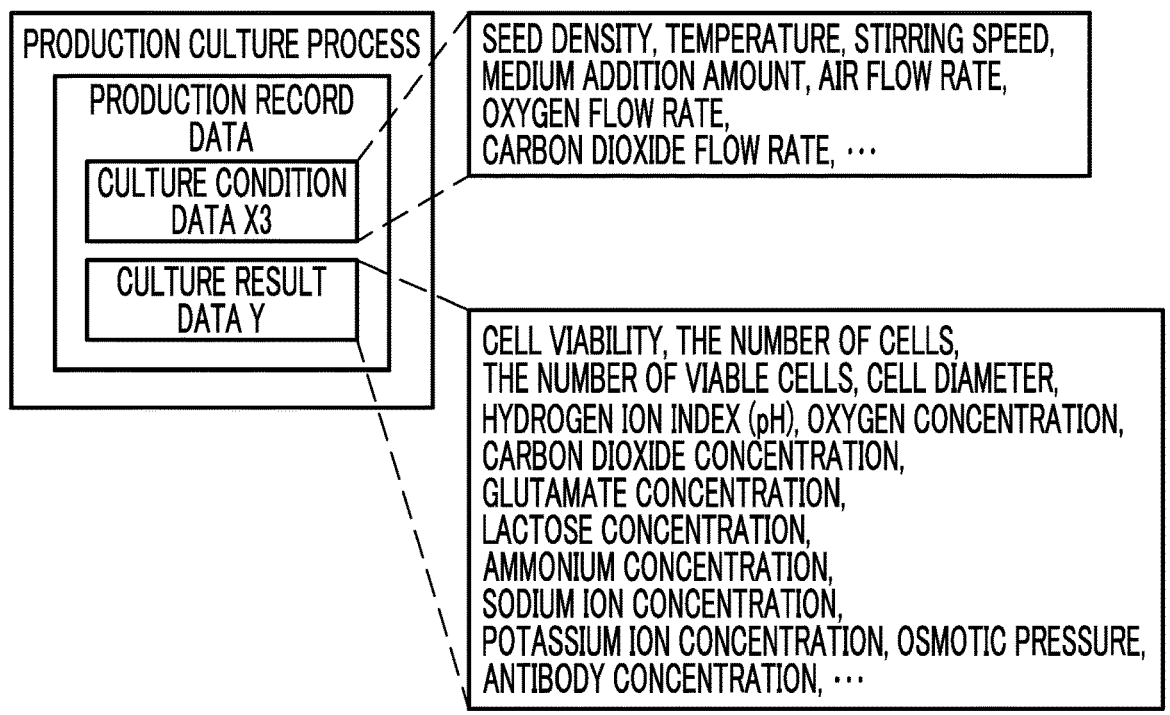
FIG. 5 is a diagram showing production record data.

As shown in FIG. 5, the production record data is a set of culture condition data X3 showing a record of culture conditions in the production culture process and culture result data Y showing a record of culture results obtained by performing cell culture with the culture condition data X3. The culture condition data X3 of the production record data is a set of respective conditions of a plurality of processes performed in the production culture process, similarly to the culture condition data X1 of the initial record data. The culture condition data X3 of the production record data includes a seed density, a temperature, a stirring rate, a medium addition amount, an air flow rate, an oxygen flow rate, a carbon dioxide flow rate, and the like, similar to the culture condition data X1 of the initial record data. In addition, the culture result data Y of the production record data includes a cell viability, the number of cells, the number of viable cells, a cell diameter, a hydrogen ion index (pH), an oxygen concentration, a carbon dioxide concentration, a glutamate concentration, a lactose concentration, an ammonium concentration, a sodium ion concentration, a potassium ion concentration, an osmotic pressure, an antibody concentration, and the like, similar to the culture result data X2 of the initial record data.

Figure 6:
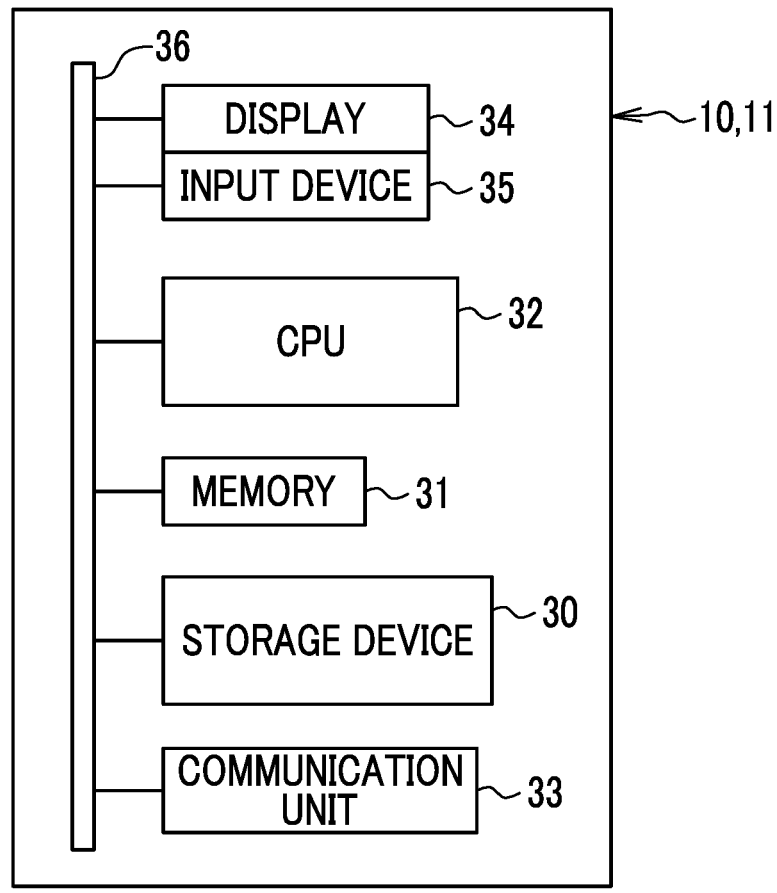
FIG. 6 is a block diagram showing a computer that configures the operator terminal and the cell culture support server.

In FIG. 6, the computers that constitute the operator terminal 10 and the cell culture support server 11 have the same basic configuration, and each computer comprises a storage device 30, a memory 31, a central processing unit (CPU) 32, a communication unit 33, a display 34, and an input device 35, respectively. These components are connected to each other through a data bus 36.

The storage device 30 is a hard disk drive that is built in the computer that constitutes the operator terminal 10 or the like or is connected to the computer through a cable or a network. Alternatively, the storage device 30 is a disk array in which a plurality of hard disk drives are connected in series. The storage device 30 stores a control program such as an operating system, various application programs, various types of data associated with these programs, and the like.

The memory 31 is a work memory used when the CPU 32 executes processing. The CPU 32 loads the program stored in the storage device 30 into the memory 31, and executes processing according to the program, thereby comprehensively controlling the respective units of the computer.

The communication unit 33 is a network interface that performs a transmission control of various types of information through the network 12. The display 34 displays various screens. Various screens are provided with an operation function by Graphical User Interface (GUI). The computer that constitutes the operator terminal 10 or the like receives an input of an operation command through the input device 35 on the various screens. The input device 35 is a keyboard, a mouse, a touch panel, or the like.

In the following description, a suffix "A" is assigned to each unit of the computer that configures the operator terminal 10, and a suffix "B" is assigned to each unit of the computer that configures the cell culture support server 11, respectively.

Figure 7:
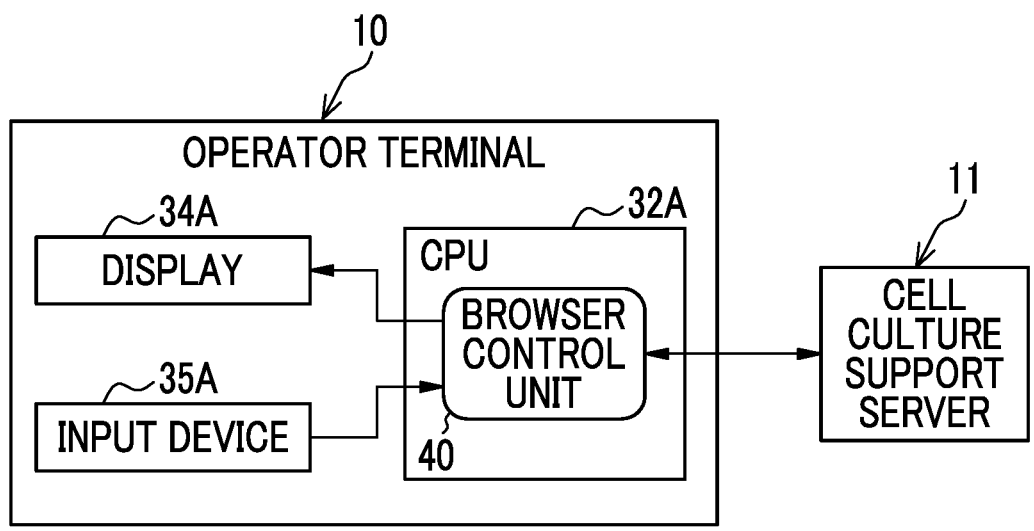
FIG. 7 is a block diagram showing a processing unit of a CPU of the operator terminal.

In FIG. 7, in a case where a web browser is activated, the CPU 32A of the operator terminal 10 functions as a browser control unit 40 in cooperation with the memory 31, and the like. The browser control unit 40 controls an operation of the web browser. The browser control unit 40 receives screen data of various screens from the cell culture support server 11. The browser control unit 40 reproduces the various screens displayed on the web browser on the basis of the screen data, and displays the various screens on a display 34A.

The browser control unit 40 also receives various operation commands input through the input device 35A on the various screens. The browser control unit 40 issues various requests corresponding to the various operation commands to the cell culture support server 11. The operation commands include a guideline information output command. In a case where the guideline information output command is received, the browser control unit 40 issues an output request for guideline information to the cell culture support server 11.

Figure 8:
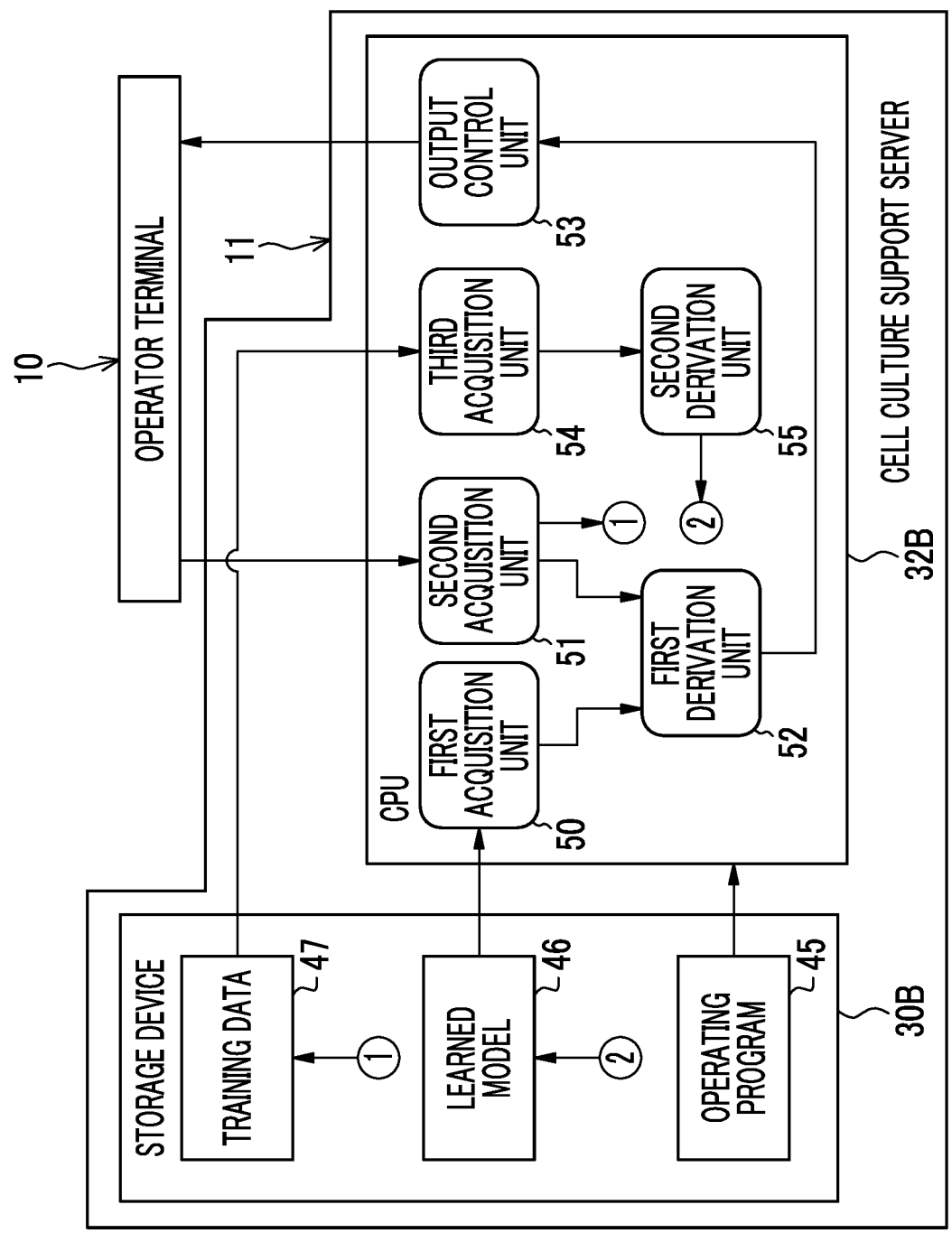
FIG. 8 is a block diagram showing a processing unit of a CPU of the cell culture support server.

In FIG. 8, a storage device 30B of the cell culture support server 11 stores an operating program 45 that is an application program. The operating program 45 is an application program for causing the computer that constitutes the cell culture support server 11 to function as a cell culture support apparatus. That is, the operating program 45 is an example of a "program for operating the cell culture support apparatus" according to the technique of the present disclosure. The storage device 30B stores a learned model 46 and training data 47 in addition to the operating program 45.

In a case where the operating program 45 is activated, the CPU 32B of the cell culture support server 11 functions as a first acquisition unit 50, a second acquisition unit 51, a first derivation unit 52, an output control unit 53, a third acquisition unit 54, and a second derivation unit 55 in cooperation with the memory 31, and the like.

In an operating phase of machine learning, the first acquisition unit 50 reads out the learned model 46 from the storage device 30B to acquire the learned model 46. The first acquisition unit 50 outputs the acquired learned model 46 to the first derivation unit 52.

In the operating phase, the second acquisition unit 51 receives the output request for the guideline information from the operator terminal 10. As described above, the output request for the guideline information includes the initial record data and the temporary culture condition data. For this reason, the second acquisition unit 51 acquires the initial record data and the temporary culture condition data by receiving the output request for the guideline information. The second acquisition unit 51 outputs the acquired initial record data and temporary culture condition data to the first derivation unit 52. The initial record data acquired by the second acquisition unit 51 and output to the first derivation unit 52 is the initial record data for analysis to be analyzed by the first derivation unit 52 using the learned model 46.

Further, in a learning phase of machine learning, the second acquisition unit 51 also receives the registration request for the initial record data from the operator terminal 10. That is, the second acquisition unit 51 acquires the initial record data by receiving the registration request for the initial record data. The second acquisition unit 51 registers the acquired initial record data in the storage device 30B as the training data 47. The initial record data acquired by the second acquisition unit 51 and registered in the storage device 30B is initial record data for learning.

Further, in the learning phase, the second acquisition unit 51 also receives the registration request for the production record data from the operator terminal 10. That is, the second acquisition unit 51 acquires the production record data by receiving the registration request for the production record data. The second acquisition unit 51 registers the acquired production record data in the storage device 30B as the training data 47. The production record data acquired by the second acquisition unit 51 and registered in the storage device 30B is the production record data for learning.

In the operating phase, the first derivation unit 52 derives guideline information from the learned model 46 acquired in the first acquisition unit 50, the initial record data for analysis acquired in the second acquisition unit 51, and the temporary culture condition data. The first derivation unit 52 outputs the derived guideline information to the output control unit 53.

In the operating phase, the output control unit 53 corresponds to a first output control unit and a second output control unit, and performs a control for outputting the guideline information from the first derivation unit 52. More specifically, the output control unit 53 generates screen data of the guideline information display screen 80 for web distribution. Then, the generated screen data of the guideline information display screen 80 is output to the operator terminal 10 that is an output request source. The output control unit 53 generates screen data of various screens other than the guideline information display screen 80, and outputs the result to the operator terminal 10.

In the learning phase, the third acquisition unit 54 reads out the training data 47 from the storage device 30B to acquire the training data 47. The training data 47 includes initial record data for learning and production record data for learning (see FIG. 10). That is, the third acquisition unit 54 acquires the training data 47 to acquire the initial record data for learning and the production record data for learning. The third acquisition unit 54 outputs the acquired training data 47 to the second derivation unit 55.

In the learning phase, the second derivation unit 55 performs machine learning on the basis of the training data 47 from the third acquisition unit 54 to derive the learned model 46. The second derivation unit 55 registers the derived learned model 46 in the storage device 30B.

The acquisition of the training data 47 in the third acquisition unit 54 and the derivation of the learned model 46 in the second derivation unit 55 are performed at preset timings such as every month. Of course, the acquisition of the training data 47 in the third acquisition unit 54 and the derivation of the learned model 46 in the second derivation unit 55 may be performed at timings commanded by the operator.

Further, the acquisition of the training data 47 in the third acquisition unit 54 and the derivation of the learned model 46 in the second derivation unit 55 are not performed while the number of samples of the training data 47 is smaller than a set value. In other words, the learned model 46 is derived by the second derivation unit 55 only in a case where the number of samples of the training data 47 is equal to or larger than the set value. The number of samples of the training data 47 is the number of records shown in FIG. 10.

Figure 9:
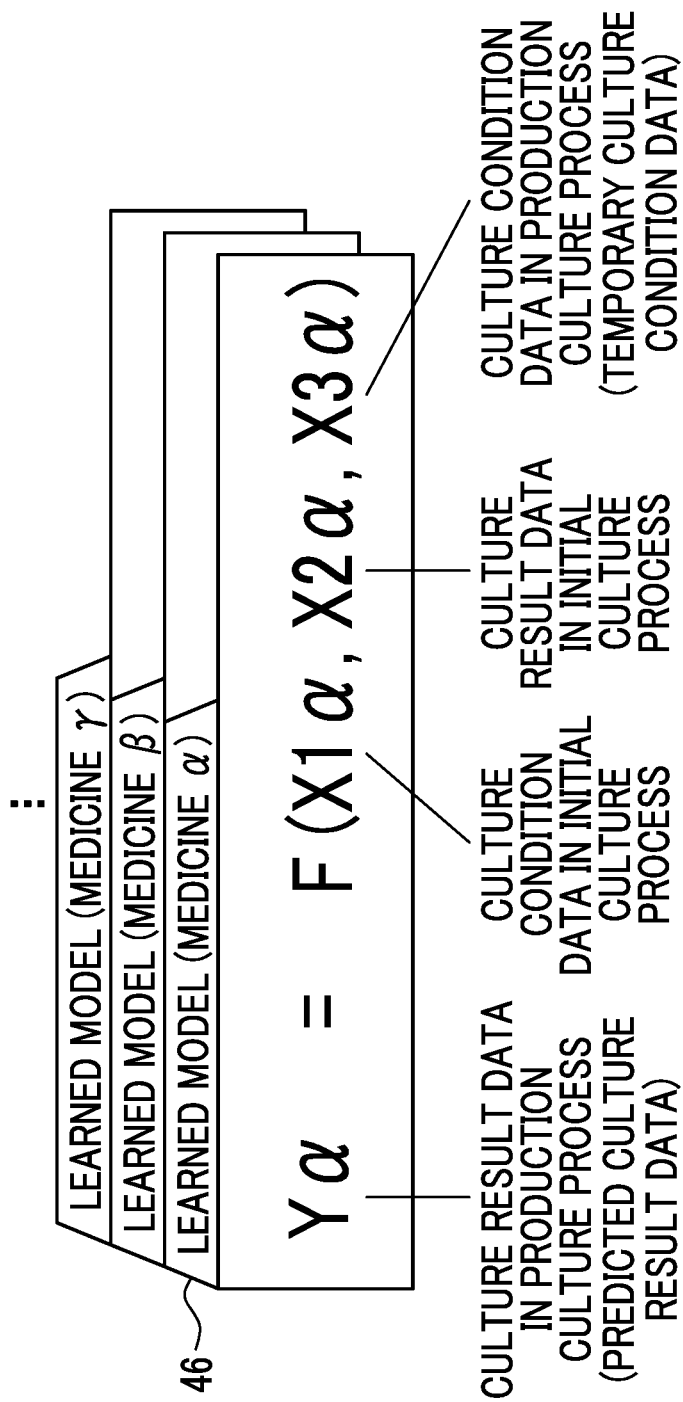
FIG. 9 is a diagram showing content of a learned model.

In FIG. 9, the learned model 46 is derived for each culture purpose such as for medicine α or medicine β.

The learned model 46 sets the culture result data Y of the production culture process as an objective variable, and sets the culture condition data X1 of the initial culture process, the culture result data X2 of the initial culture process, and the culture condition data X3 of the production culture process as explanatory variables. The first derivation unit 52 inputs the initial record data for analysis from the second acquisition unit 51, that is, the culture condition data and the culture result data in the initial culture process, and the temporary culture condition data into the learned model 46 for calculation to derive predicted culture result data. In FIG. 9, the learned model 46 for the medicine a is shown. Accordingly, each variable is assigned a suffix α as in "Yα".

In FIG. 10, the training data 47 is registered for each culture purpose, similar to the learned model 46. In the training data 47, an area separated by a culture ID that is assigned to each cell culture from the initial culture process to the production culture process forms one record. The culture condition data X1 and the culture result data X2 in the initial culture process, that is, the initial record data for learning, and the culture condition data X3 and the culture result data Y in the production culture process, that is, the production record data for learning are registered in one record. That is, the training data 47 includes the initial record data for learning and the production record data for learning. Note that FIG. 10 shows the training data 47 for the medicine α in a similar way to FIG. 9. A numeral after an underscore in each piece of data indicates a culture ID. For example, culture condition data of initial record data of a culture ID "001" is represented as "X1α_001".

The initial record data for learning and the production record data for learning are input by an operator, for example, through an input screen (not shown) displayed on the display 34A of the operator terminal 10. The culture purpose and the culture ID are also input at this time. The input screen is generated in the output control unit 53 of the cell culture support server 11, and is output to the operator terminal 10. Then, the input screen is displayed on the display 34A by the browser control unit 40 of the operator terminal 10.

The input screen is provided with a send button for performing a command for transmitting the input initial record data for learning or the production record data for learning to the cell culture support server 11. In a case where this send button is selected, the browser control unit 40 issues a registration request for the initial record data for learning or a registration request for the production record data for learning to the cell culture support server 11.

The initial record data for learning is input at the end of the initial culture process, for example, and the production record data for learning is input at the end of the production culture process, for example. The culture condition data and the culture result data in an intermediate culture process between the initial culture process and the production culture process are not input, and therefore, the culture condition data and the culture result data in the intermediate culture process are not registered in the training data 47.

FIG. 11 shows an example of an input screen 60 for performing an output request for guideline information, which is displayed on the display 34A of the operator terminal 10. The input screen 60 is generated in the output control unit 53 of the cell culture support server 11, and is output to the operator terminal 10. Then, the input screen 60 is displayed on the display 34A by the browser control unit 40 of the operator terminal 10.

A first area 61, a second area 62, a third area 63, a fourth area 64, and an OK button 65 are provided on the input screen 60. An input box 66 for the culture purpose is input to the first area 61, an input box 67 for the culture condition data X1 in the initial culture process is input to the second area 62, an input box 68 for the culture result data X2 in the initial culture process is input to the third area 63, and an input box 69 for the temporary culture condition data in the production culture process is input to the fourth area 64. As shown in FIGS. 4 and 5, the reason why the plurality of input boxes 67 to 69 are respectively prepared is that there are a plurality of types of data in the culture condition data X1 in the initial culture process, the culture result data X2 in the initial culture process, and the culture result data Y in the production culture process, respectively.

A reference button 70 is provided next to the second area 62. The reference button 70 is selected in a case where it is necessary to input the culture condition data X1 in the initial culture process, which has been requested to be registered in advance and has already been registered in the training data 47, in the input box 67. In a case where the reference button 70 is selected, the culture condition data X1 in the initial culture process registered in the training data 47 is displayed in a list on the input screen 60 together with the culture ID, and the like. The operator selects the culture condition data X1 in the initial culture process to be input from the list. Then, the selected culture condition data X1 in the initial culture process is read out from the training data 47, and is input to the input box 67.

A reference button 71 is also provided next to the third area 63. The reference button 71 is also selected in a case where it is necessary to input the culture result data X2 in the initial culture process that has already been registered in the training data 47 to the input box 68, similarly to the reference button 70.

A data set button 72 is provided next to the fourth area 64. The data set button 72 is selected in a case where a plurality of pieces of preset temporary culture condition data are input as the temporary culture condition data. The plurality of pieces of temporary culture condition data are, for example, five pieces of data in which the temperature among the culture condition data in the production culture process is changed in steps of 2.5° C. and the remaining data except for the temperature is the same. Alternatively, the plurality of pieces of temporary culture condition data are 10 pieces of data in which values of certain 3 types of data among the culture condition data in the production culture process are randomly changed and values of data other than the certain 3 types of data are the same. The plurality of pieces of temporary culture condition data may be fixed, or may be configured so that the operator can change their settings. In addition, the plurality of pieces of temporary culture condition data may be set on the basis of design of experiments.

The culture purpose is input to the input box 66, the culture condition data X1 in the initial culture process is input to the input box 67, the culture result data X2 in the initial culture process is input to the input box 68, and the temporary culture condition data in the production culture process is input to the input box 69, and then, the OK button 65 is selected. In this case, the browser control unit 40 issues an output request for predicted culture result data to the cell culture support server 11.

The culture purpose is input to the input box 66, the culture condition data X1 in the initial culture process is input to the input box 67, the culture result data X2 in the initial culture process is input to the input box 68, and then, the data set button 72 is selected and the OK button 65 is selected. In this case, the browser control unit 40 issues an output request for the best temporary culture condition data to the cell culture support server 11.

Figure 12:
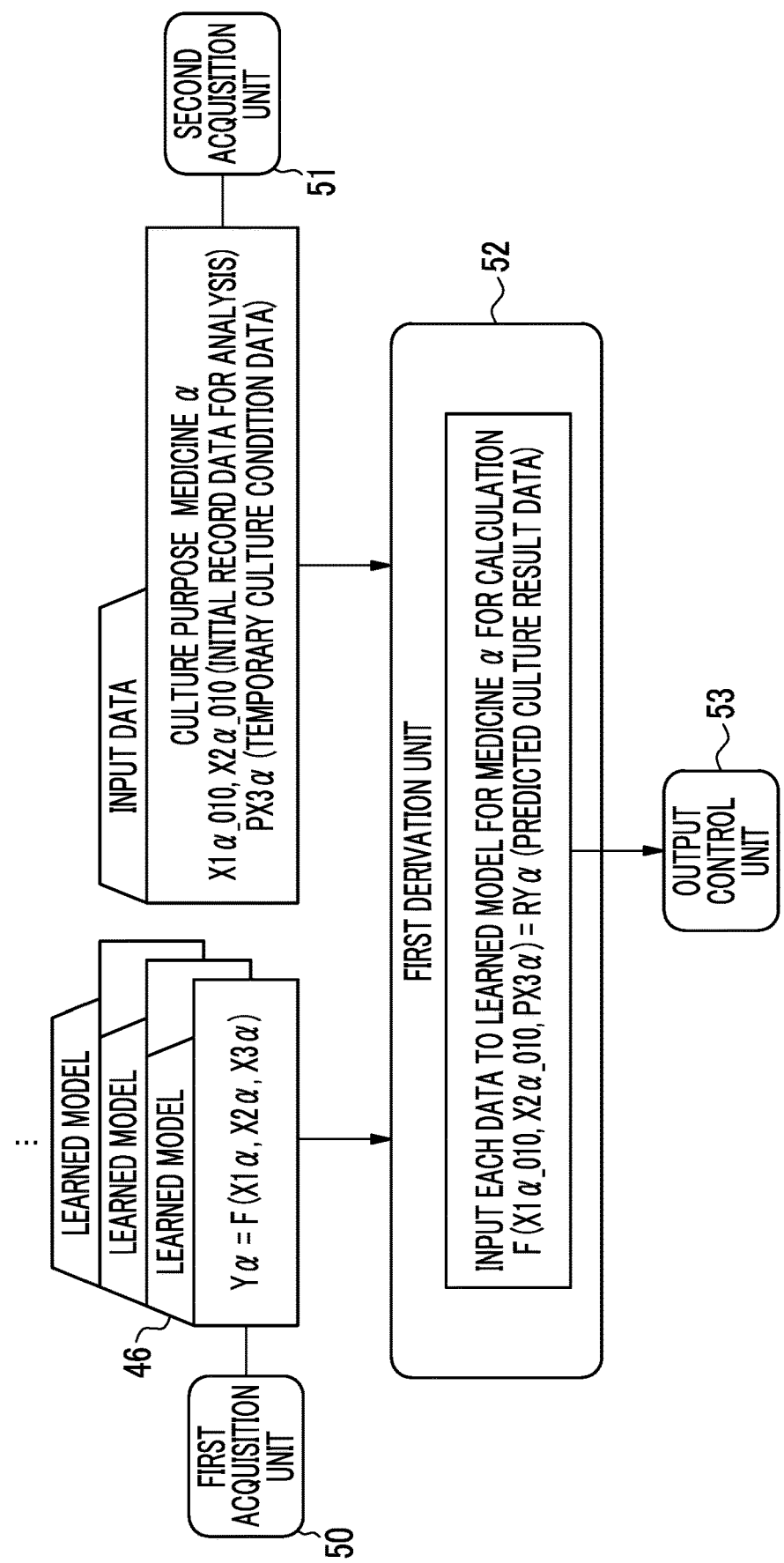
FIG. 12 is a diagram showing a deriving process of predicted culture result data in a first derivation unit.
Figure 13:
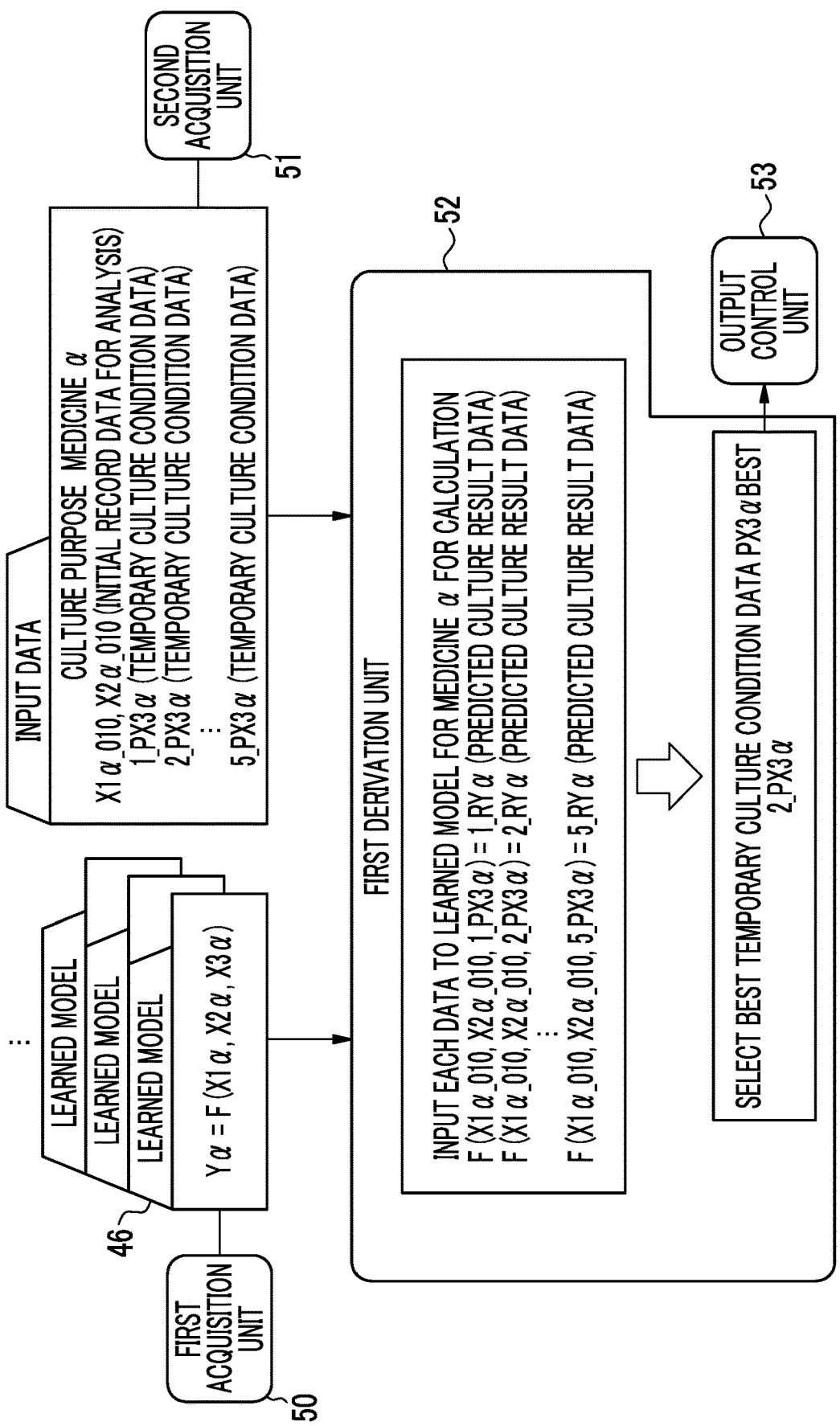
FIG. 13 is a diagram showing a deriving process of the best temporary culture condition data in the first derivation unit.

FIGS. 12 and 13 are diagrams showing a guideline information deriving process in the first derivation unit 52. FIG. 12 shows a deriving process of the predicted culture result data, and FIG. 13 shows a deriving process of the best temporary culture condition data.

FIG. 12 shows a case where the medicine α is input to the input box 66 for the culture purpose, culture condition data X1α_010 in the initial culture process is input to the input box 67, culture result data X2α_010 in the initial culture process is input to the input box 68, and temporary culture condition data PX3α in the production culture process is input to the input box 69. In this case, the first derivation unit 52 inputs the culture condition data X1α_010 in the initial culture process, the culture result data X2α_010 in the initial culture process, and the temporary culture condition data PX3α to Yα=F (X1α, X2α, X3α), which is the learned model 46 for the medicine a, for calculation. As a result, predicted culture result data RYα is obtained. The first derivation unit 52 outputs the predicted culture result data RYα to the output control unit 53 as guideline information.

FIG. 13 shows a case where the medicine α is input to the input box 66 for the culture purpose, the culture condition data X1α_010 in the initial culture process is input to the input box 67, and the culture result data X2α_010 in the initial culture process is input to the input box 68, similarly to FIG. 12. However, FIG. 13 shows a case where the data set button 72 is selected and a total of five pieces of temporary culture condition data of preset 1_PX3α, 2_PX3α, . . . , and 5_PX3α are input. In this case, the first derivation unit 52 derives predicted culture result data for each of the temporary culture condition data 1_PX3α to 5_PX3α. More specifically, the first derivation unit 52 inputs the culture condition data X1α_010 in the initial culture process, the culture result data X2α_010 in the initial culture process, and the temporary culture condition data 1_PX3α to Yα=F (X1α, X2α, X3α), which is the learned model 46 for the medicine α, for calculation. As a result, predicted culture result data 1_RYα is obtained. Similarly, the first derivation unit 52 inputs the temporary culture condition data 2_PX3α for calculation to obtain predicted culture result data 2_RYα, . . . , and inputs the temporary culture condition data 5_PX3α for calculation to obtain predicted culture result data 5_RYα. Here, the notation of " . . . " including that in the figures means omission.

Subsequently, the first derivation unit 52 selects the best temporary culture condition data PX3αBEST having the best predicted culture result data from the temporary culture condition data 1_PX3α to 5_PX3α. FIG. 13 shows a case where the predicted culture result data 2_RYα is the best among the obtained predicted culture result data 1_RYα to 5_RYα and the temporary culture condition data 2_PX3α is selected as the best temporary culture condition data PX3αBEST. To give a more specific example, the first derivation unit 52 obtains the antibody concentration as the predicted culture result data RY, and selects the temporary culture condition data PX3 having the highest antibody concentration as the best temporary culture condition data PX3BEST. The first derivation unit 52 outputs the best temporary culture condition data 2_PX3α to the output control unit 53 as guideline information.

Figure 14:
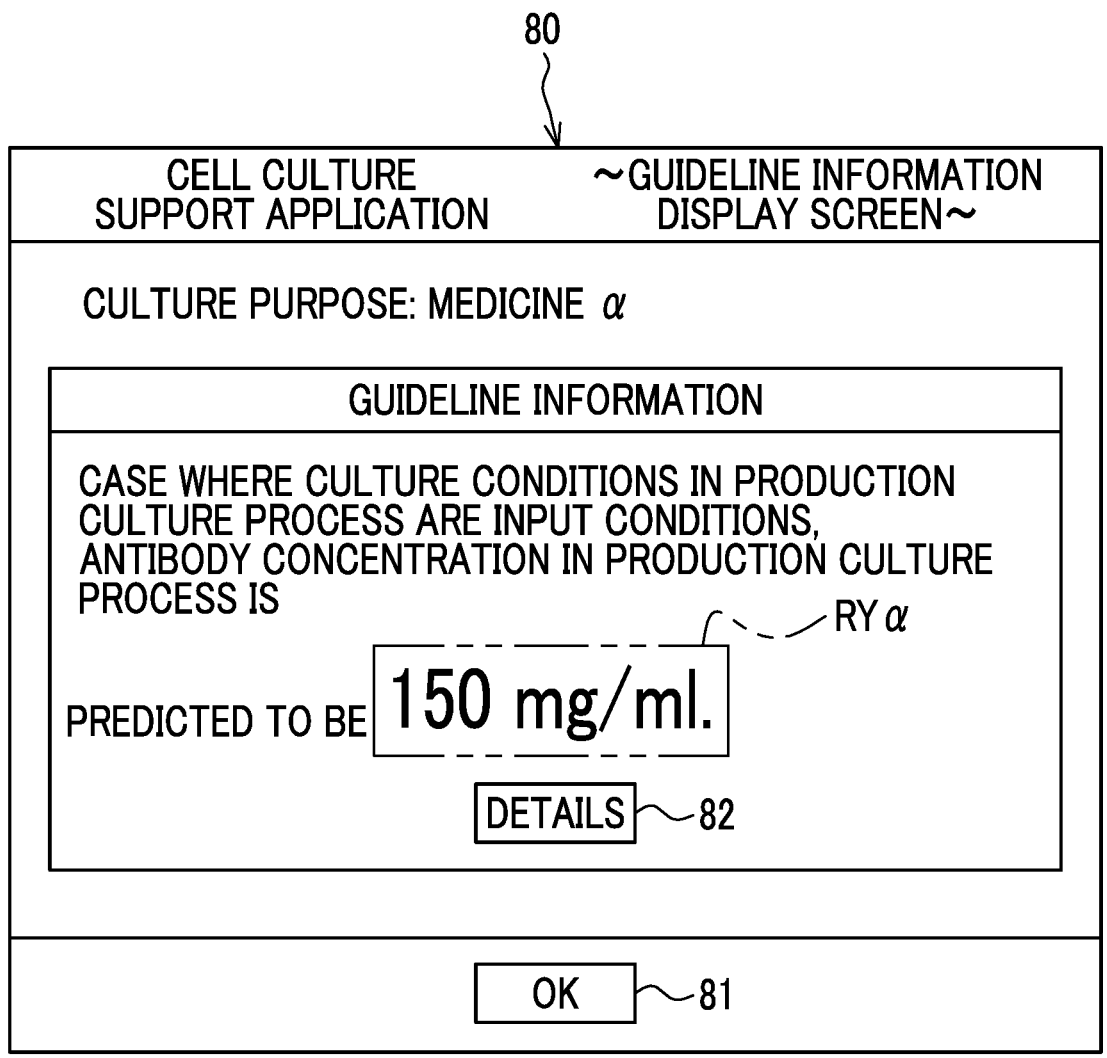
FIG. 14 is a diagram showing a guideline information display screen.
Figure 15:
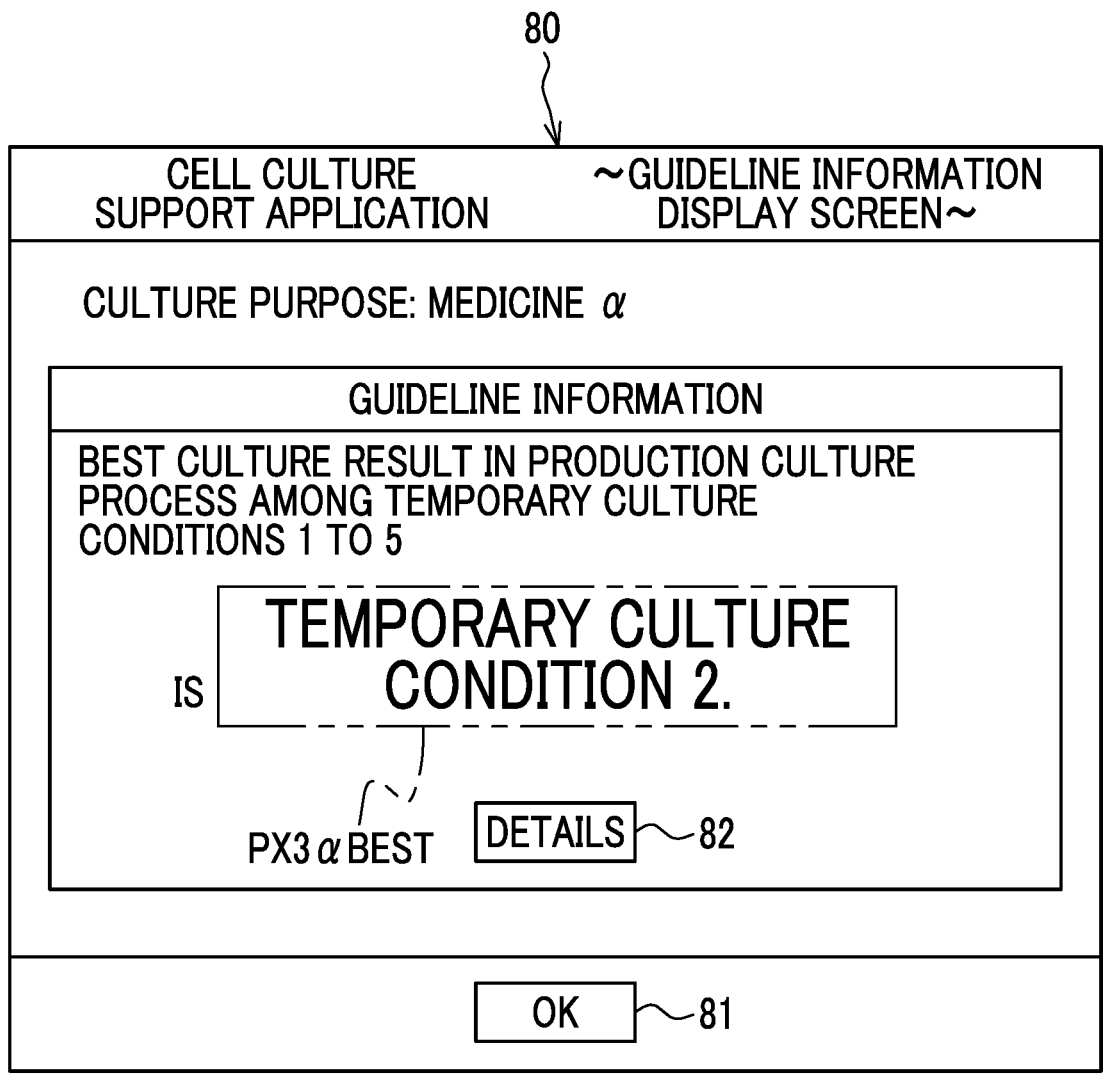
FIG. 15 is a diagram showing a guideline information display screen.

FIGS. 14 and 15 show examples of the guideline information display screen 80 displayed on the display 34A of the operator terminal 10. The guideline information display screen 80 is generated in the output control unit 53 of the cell culture support server 11, and is output to the operator terminal 10. Then, the guideline information display screen 80 is displayed on the display 34A by the browser control unit 40 of the operator terminal 10. The display of the guideline information display screen 80 disappears in a case where the OK button 81 is selected.

The guideline information display screen 80 shown in FIG. 14 is an example in which the predicted culture result data RYα (here, the antibody concentration) is displayed as the guideline information. More specifically, a sentence "In a case where the culture conditions in the production culture process are input conditions, the antibody concentration in the production culture process is predicted to be 150 mg/ml" is displayed as guideline information. In the sentence, "150 mg/ml" is the predicted culture result data RYα.

The guideline information display screen 80 shown in FIG. 15 is an example in which the best temporary culture condition data PX3αBEST is displayed as guideline information. More specifically, a sentence "The best culture result in the production culture process among the temporary culture conditions 1 to 5 is a temporary culture condition 2." is displayed as guideline information. In the sentence, the "temporary culture condition 2" is the best temporary culture condition data PX3αBEST. On the guideline information display screen 80 shown in FIG. 15, in addition to the best temporary culture condition data PX3BEST, the predicted culture result data RY in the case of the best temporary culture condition data PX3BEST may be displayed. In addition, for example, by displaying a plurality of pieces of temporary culture condition data PX3 and its predicted culture result data RY in a list, and displaying the best temporary culture condition data PX3BEST in a shaded manner, the display may be performed to be distinguished from display of other temporary culture condition data PX3.

A detail button 82 for displaying details of guideline information is provided on the guideline information display screen 80. In a case where the detail button 82 is selected on the guideline information display screen 80 shown in FIG. 14, detailed content and the like of the temporary culture condition data PX3α input through the input screen 60 are displayed. In a case where the detail button 82 is selected on the guideline information display screen 80 shown in FIG. 15, detailed content and the like of the best temporary culture condition data PX3αBEST are displayed.

Figure 16:
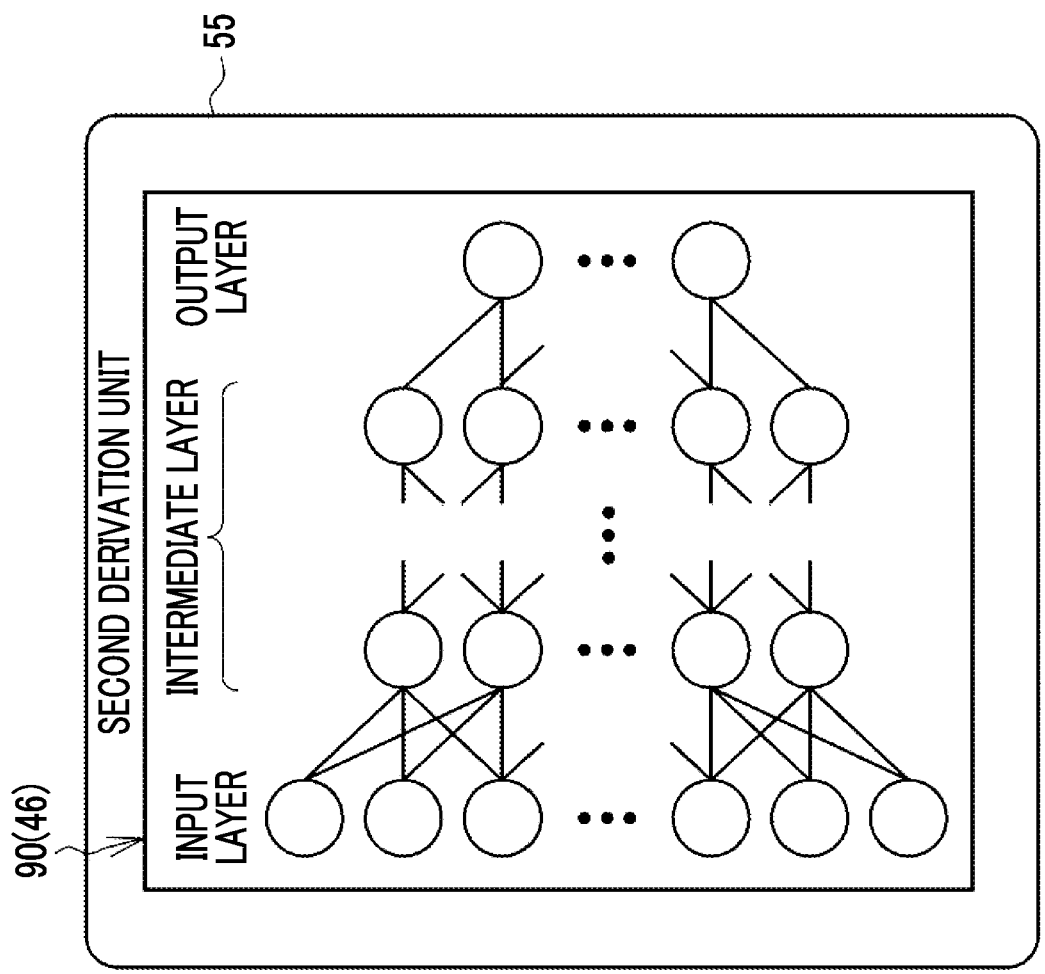
FIG. 16 is a diagram showing a state where a learned model is derived in a second derivation unit.

As shown in FIG. 16, the second derivation unit 55 uses a neural network 90 as a machine learning method for deriving the learned model 46, for example. The neural network 90 includes an input layer, a plurality of intermediate layers (hidden layers), and an output layer, as shown as an example. The neural network 90 is an estimation model for simulating the culture result data Y in the production culture process from the culture condition data X1 in the initial culture process, the culture result data X2 in the initial culture process, and the culture condition data X3 in the production culture process. A set of the culture condition data X1 in the initial culture process, the culture result data X2 in the initial culture process, and the culture condition data X3 in the production culture process is input to the input layer of the neural network 90. The culture result data Y in the production culture process corresponding to the above data set input to the input layer is output to the output layer of the neural network 90.

The second derivation unit 55 causes the neural network 90 to perform learning using the training data 47 according to a backpropagation method as an example of machine learning. Specifically, the second derivation unit 55 inputs the set of the culture condition data X1 in the initial culture process, the culture result data X2 in the initial culture process, and the culture condition data X3 in the production culture process included in one record of the training data 47 to the neural network 90, and outputs the culture result data Y in the production culture process from the neural network 90. Then, the second derivation unit 55 causes the neural network 90 to perform learning so that a difference between the culture result data Y in the production culture process output to the neural network 90 and the culture result data Y in the actual production culture process registered in the training data 47 is minimized.

An output value of the neural network 90 is, for example, a sum of output values output by respective nodes of respective layers according to an input value. Each node in the input layer, the intermediate layers, and the output layer is assigned a weight with respect to an input value. For example, each node is set to have a threshold value to be compared with the input value. In this case, in each node, the input value to each node is compared with the threshold value, and an output value of "0" or "1" is output according to the comparison result. In addition, a sigmoid function may be set for each node. In this case, the output value changes between "0" and "1" according to the input value. A coefficient of the threshold value or the sigmoid function for each node may be given as the weight for the input value input to each node.

The second derivation unit 55 changes the weight of the node so that the difference between the culture result data Y in the production culture process output to the neural network 90 and the culture result data Y in the actual production culture process registered in the training data 47 is minimized. The second derivation unit 55 registers the neural network 90 adjusted so that the above difference is minimized by changing the weights of the nodes in this way in the storage device 30B as the learned model 46.

Figure 17:
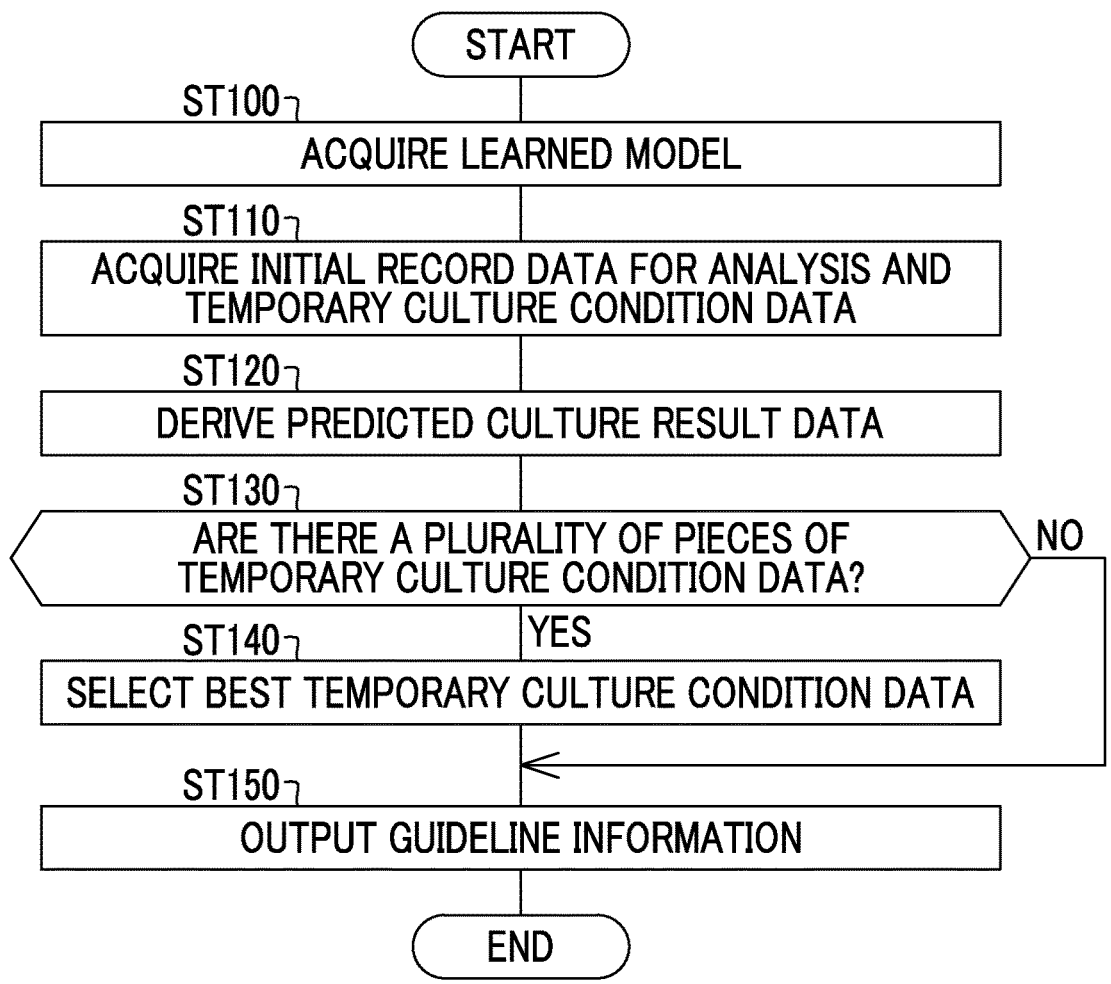
FIG. 17 is a flowchart showing a processing procedure of the cell culture support server.
Figure 18:
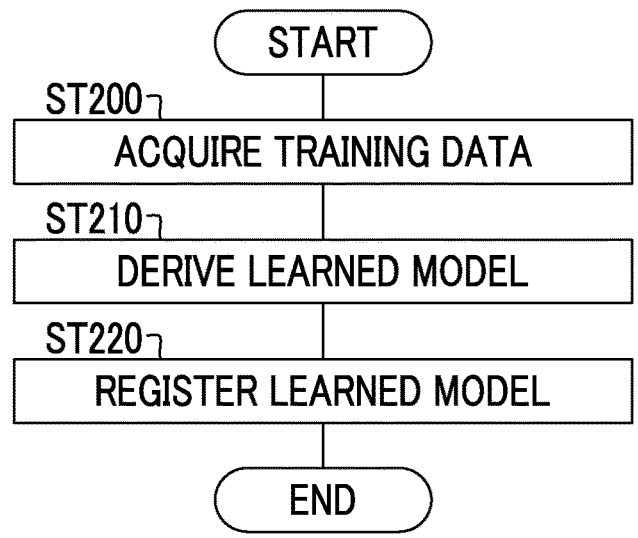
FIG. 18 is a flowchart showing a processing procedure of the cell culture support server.
Figure 19:
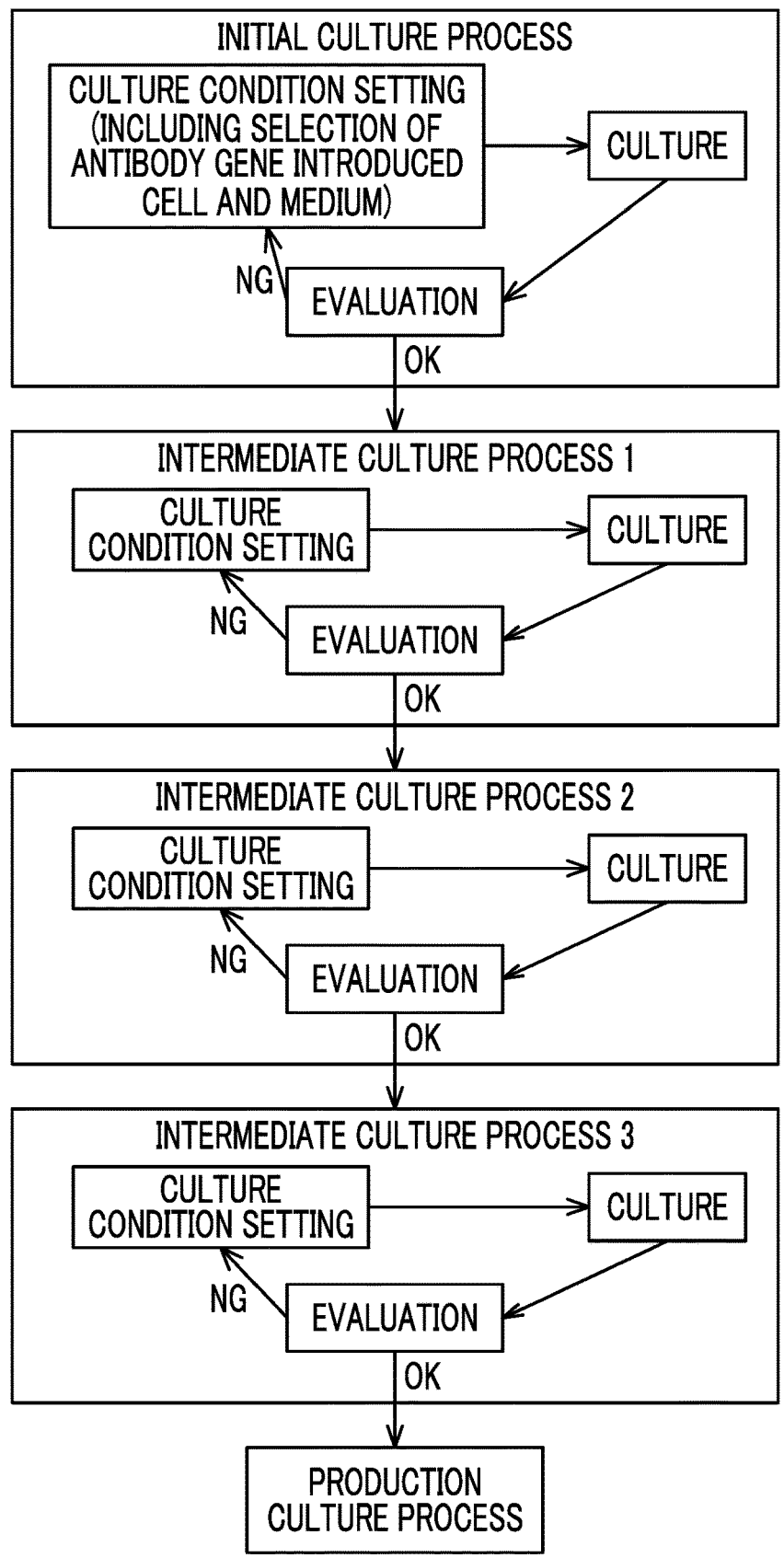
FIG. 19 is a diagram showing a cell culture procedure.

Hereinafter, an operation based on the above configuration will be described with reference to flowcharts of FIGS. 17 and 18. FIG. 17 shows an operating phase of machine learning, and FIG. 18 shows a learning phase of the machine learning.

First, as shown in FIG. 17, in the cell culture support server 11, the learned model 46 is read out from the storage device 30B to the first acquisition unit 50, so that the learned model 46 is acquired by the first acquisition unit 50 (step ST100, a first acquisition step). The learned model 46 is output from the first acquisition unit 50 to the first derivation unit 52.

In the operator terminal 10, the input screen 60 shown in FIG. 11 is displayed on the display 34A by the browser control unit 40. Then, the culture purpose, the culture condition data X1 in the initial culture process, the culture result data X2 in the initial culture process, and the temporary culture condition data PX3 in the production culture process are input through the input screen 60. Each input data is transmitted to the cell culture support server 11 as an output request for guideline information. Thus, the second acquisition unit 51 acquires the culture condition data X1 in the initial culture process, the culture result data X2 in the initial culture process, that is, initial record data for analysis, and the temporary culture condition data PX3 in the production culture process (step ST110, a second acquisition step). Each data is output from the second acquisition unit 51 to the first derivation unit 52.

In the first derivation unit 52, as shown in FIGS. 12 and 13, the predicted culture result data RY is derived (step ST120, a first derivation step). More specifically, the predicted culture result data RY is derived by inputting each data into the learned model 46 for calculation. The predicted culture result data RY is output from the first derivation unit 52 to the output control unit 53.

In a case where there are a plurality of pieces of temporary culture condition data PX3 acquired in step ST110 (YES in Step ST130), the first derivation unit 52 selects the best temporary culture condition data PX3BEST as shown in FIG. 13 (step ST140). More specifically, in step ST120, the predicted culture result data RY is derived for each of the plurality of pieces of temporary culture condition data PX3, and the best temporary culture condition data PX3BEST is selected from the plurality of pieces of temporary culture condition data PX3. The best temporary culture condition data PX3BEST is output from the first derivation unit 52 to the output control unit 53.

In the output control unit 53, screen data of the guideline information display screen 80 shown in FIGS. 14 and 15 is generated. The screen data of the guideline information display screen 80 is output to the operator terminal 10 that is an output request source by the output control unit 53 (Step ST150).

In the operator terminal 10, the guideline information display screen 80 from the cell culture support server 11 is displayed on the display 34A by the browser control unit 40. The operator browses the guideline information displayed on the guideline information display screen 80, and performs the culture work according to the guideline information. For example, in a case where the guideline information display screen 80 shown in FIG. 15 is displayed, the operator starts the production culture process under the temporary culture condition 2.

The predicted culture result data RY in the production culture process is derived by the first derivation unit 52 using the learned model 46 showing a relationship between the initial culture process and the production culture process, and using the culture condition data X1 in the initial culture process, the culture result data X2 in the initial culture process, and the temporary culture condition data PX3. Accordingly, it is possible to predict a culture result in the production culture process without data in an intermediate culture process. Accordingly, it is possible to save an effort for carrying out the intermediate culture process, and thus, to significantly reduce a period from the initial culture process to the production culture process in the cell culture.

Since the predicted culture result data RY is output by the output control unit 53 to be provided to an operator for viewing, it is possible for the operator to easily know what the predicted culture result data RY will be in the temporary culture condition data PX3 input by the operator.

In a case where a plurality of pieces of temporary culture condition data PX3 are acquired by the second acquisition unit 51, the first derivation unit 52 derives the predicted culture result data RY for each of the plurality of pieces of temporary culture condition data PX3, and selects the best temporary culture condition data PX3BEST from the plurality of pieces of temporary culture condition data PX3. Accordingly, it is possible for the operator to easily know the best temporary culture condition data PX3BEST. Further, in a case where the culture conditions in the production culture process are set according to the best temporary culture condition data PX3BEST, relatively good culture result data Y is promised, and thus, medicine production efficiency is also improved.

As shown in FIG. 18, in the cell culture support server 11, the training data 47 is read out from the storage device 30B to the third acquisition unit 54 at a preset timing, so that the training data 47 is acquired by the third acquisition unit 54 (step ST200). The training data 47 is output from the third acquisition unit 54 to the second derivation unit 55.

In the second derivation unit 55, as shown in FIG. 16, the neural network 90 performs learning by the training data 47, and thus, the learned model 46 is derived (step ST210). The learned model 46 is registered in the storage device 30B by the second derivation unit 55 (step ST220).

In this way, since the third acquisition unit 54 acquires the training data 47 and the second derivation unit 55 derives the learned model 46 on the basis of the training data 47, it is possible to update the learned model 46 according to the training data 47 that is constantly updated. Further, it is possible to save an effort for providing the learned model 46 from another computer.

In the above embodiment, an example in which the learned model 46 and the training data 47 are registered in the storage device 30B of the cell culture support server 11 is shown, but the present disclosure is not limited thereto. A configuration in which the learned model 46 and the training data 47 are registered in a database server different from the cell culture support server 11 and the learned model 46 and the training data 47 are transmitted from the database server to the cell culture support server 11 may be used.

In the above embodiment, an example in which various screens such as the guideline information display screen 80 are output from the output control unit 53 to the operator terminal 10 in the form of screen data for web distribution is shown, but the present disclosure is not limited thereto. A configuration in which an application program for displaying various screens is installed in the operator terminal 10 and a command for instructing the application program to display various screens is output from the output control unit 53 may be used.

The output form of the guideline information is not limited to the guideline information display screen 80 of the above embodiment. The guideline information may be printed by a printer connected to the operator terminal 10, or a file indicating the guideline information may be transmitted to the operator terminal 10 by e-mail.

The machine learning method is not limited to the neural network 90. Other methods such as a regression tree or a classification tree may be used.

In the above embodiment, an example in which the initial culture process is a process of selecting cells into which an antibody gene has been introduced and a medium and the production culture process is a process of producing an antibody-based medicine is shown, but the present disclosure limited thereto. As long as the production culture process is at least a process performed in a facility larger than the initial culture process, the present disclosure may be applied.

Various modifications may be made to the hardware configuration of the computer that configures the cell culture support server 11. For example, the cell culture support server 11 may be configured of a plurality of server computers separated as hardware for the purpose of improving processing capacity and reliability. Specifically, the functions of the first acquisition unit 50, the second acquisition unit 51, the first derivation unit 52, and the output control unit 53, the functions of the third acquisition unit 54 and the second derivation unit 55 may be assigned to two server computers in a distributed manner. In this case, the cell culture support server 11 is configured by two server computers.

In the above embodiment, the output control of the predicted culture result data RY and the output control of the best temporary culture condition data PX3BEST are assigned to one output control unit 53, but the present disclosure is not limited to thereto. A configuration in which a first output control unit that performs a control for outputting the predicted culture result data RY and a second output control unit that performs a control for outputting the best temporary culture condition data PX3BEST are dividedly provided may be used.

Further, a configuration in which the operating program 45 is installed in the operator terminal 10, each processing unit built in the cell culture support server 11 in the above embodiment is built in the operator terminal 10, and the operator terminal 10 is operated as the cell culture support apparatus may be used.

In this way, the hardware configuration of the computer may be appropriately modified according to necessary performance such as processing capacity, security, and reliability. Further, as well as the hardware, the application program such as the operating program 45 may be duplicated or stored in a plurality of storage devices in a distributed manner for the purpose of ensuring security and reliability.

In the above embodiment, a configuration in which the cell culture support server 11 is installed and used in one cell culture laboratory is shown, but a configuration in which the cell culture support server 11 is used in a plurality of cell culture laboratories may be used. In order to make the cell culture support server 11 available in a plurality of cell culture laboratories, the cell culture support server 11 is connected to a plurality of operator terminals 10 installed in the plurality of cell culture laboratories through a wide area network (WAN) such as the Internet or a public communication network in a communicable manner. Then, the cell culture support server 11 receives an output request from each operator terminal 10 through the WAN, and outputs guideline information to each operator terminal 10. In this case, an installation location and an operating party of the cell culture support server 11 may be, for example, a data center operated by a company other than the cell culture laboratories, or one of the plurality of cell culture laboratories.

In the above embodiment, for example, as a hardware structure of processing units that execute various processes, such as the first acquisition unit 50, the second acquisition unit 51, the first derivation unit 52, the output control unit 53, the third acquisition unit 54, and the second derivation unit 55, the following various processors may be used. As described above, in addition to the CPU 32B that is a general-purpose processor that executes software (operating program 45) to function as various processing units, various processors include a programmable logic device (PLD) that is a processor of which a circuit configuration is changeable after manufacturing, such as a field programmable gate array (FPGA), a dedicated electrical circuit that is a processor having a circuit configuration specifically designed to execute a specific process, such as an application specific integrated circuit (ASIC), or the like.

One processing unit may be configured by one of these various processors, or may be configured by a combination of two or more processors of the same type or different types (for example, a combination of a plurality of FPGAs and/or a combination of a CPU and an FPGA). Further, a plurality of processing units may be configured by one processor.

As an example in which the plurality of processing units is configured by one processor, first, as represented by a computer such as a client and a server, there is a configuration in which one processor is configured by a combination of one or more CPUs and software and the processor functions as a plurality of processing units. Secondly, as represented by a system on chip (SoC) or the like, there is a configuration in which a processor that realizes the functions of the entire system including a plurality of processing units by one integrated circuit (IC) chip is used. As described above, the various processing units are configured using one or more of the above various processors as a hardware structure.

Further, as a hardware structure of these various processors, more specifically, electric circuitry in which circuit elements such as semiconductor elements are combined may be used.

From the above description, the disclosure described in Supplementary note 1 below can be understood.

[Supplementary Note 1]

A cell culture support apparatus for supporting cell culture from an initial culture process to a production culture process performed in a facility larger than the initial culture process, the apparatus comprising: a first acquisition processor that acquires a learned model indicating a relationship between the initial culture process and the production culture process, derived by performing machine learning on the basis of initial record data for learning including a set of culture condition data indicating a record of culture conditions and culture result data indicating a record of culture results in the initial culture process, and production record data for learning, corresponding to the initial record data for learning and including a set of culture condition data indicating a record of culture conditions and culture result data indicating a record of culture results in the production culture process; a second acquisition processor that acquires initial record data for analysis including a set of the culture condition data indicating the record of the culture conditions and the culture result data indicating the record of the culture results in the initial culture process, and temporary culture condition data indicating temporary culture conditions in the production culture process; and a first derivation processor that derives predicted culture result data obtained by predicting the culture result data in the production culture process, from the learned model acquired in the first acquisition processor, and the initial record data for analysis and the temporary culture condition data acquired in the second acquisition processor.

The technique of the present disclosure may be appropriately combined with the above-described various embodiments and various modifications. Further, it is needless to say that the above embodiments are not limiting and various configurations may be adopted within a scope without departing from the concept of the present disclosure. Furthermore, the technique of the present disclosure extends to a storage medium that stores the program in a non-temporary manner, in addition to the program.

The above-described content and the above-illustrated content are detailed descriptions of portions related to the technique of the present disclosure, which are merely an example of the technique of the present disclosure. For example, the description of the above configurations, functions, operations, and effects is an example of description of configurations, functions, operations, and effects of portions related to the technique of the present disclosure. Therefore, within the scope without departing from the concept of the technique of the present disclosure, unnecessary portions may be removed, new elements may be added or replaced for the above-described content and the above-illustrated content. In addition, in order to avoid complication and facilitate understanding of the portions related to the technique of the present disclosure, in the above-described content and the above-illustrated content, description of common knowledge or the like that does not need special explanation in implementing the technique of the present disclosure is omitted.

In the present specification, "A and/or B" is synonymous with "at least one of A or B". That is, "A and/or B" may refer to only A, only B, or a combination of A and B. In addition, in the present specification, the same concept as "A and/or B" is also applied to a case where three or more matters are linked by "and/or".

All documents, patent applications and technical standards disclosed in this specification are incorporated in this specification by reference in such a manner that the incorporation by reference of individual document, patent application and technical standard are handled to the same extent as in specific and individual description thereof

What is claimed is:

1. A non-transitory computer-readable storage medium storing a program for operating a cell culture support apparatus for supporting cell culture from an initial culture process, wherein cells into which an antibody gene has been introduced for a production of an antibody-based medicine is cultured using a culture medium, to a production culture process, wherein the cells are cultured using the culture medium, performed in a facility larger than the initial culture process, the program causing a computer to be programmed to function as:

a first acquisition unit that acquires a learned model indicating a relationship between the initial culture process and the production culture process, derived by performing machine learning on the basis of initial record data for learning including a set of culture condition data indicating a record of culture conditions in the initial culture process and culture result data indicating a record of culture results at the end of the initial culture process, and production record data for learning, corresponding to the initial record data for learning and including a set of culture condition data indicating a record of culture conditions in the production culture process and culture result data indicating a record of culture results at the end of the production culture process;

a second acquisition unit that acquires initial record data for analysis including a set of the culture condition data indicating the record of the culture conditions and the culture result data indicating the record of the culture results in the initial culture process, and temporary culture condition data indicating temporary culture conditions in the production culture process; and
a first derivation unit that derives predicted culture result data obtained by predicting the culture result data in the production culture process, from the learned model acquired in the first acquisition unit, and the initial record data for analysis and the temporary culture condition data acquired in the second acquisition unit,
wherein the learned model is acquired by performing machine learning using the culture result data of the production culture process as an objective variable and using the initial record data for learning and the culture condition data of the production culture process as explanatory variables,
the predicted culture result data, which is the target variable output by the learned model, is derived by inputting initial record data for analysis and the temporary culture condition as the explanatory variables into the learned model, and
the culture result data and the predicted culture result data include any one of a cell viability, the number of cells, the number of viable cells, a cell diameter, a hydrogen ion index, an oxygen concentration, a carbon dioxide concentration, a glutamate concentration, a lactose concentration, an ammonium concentration, a sodium ion concentration, a potassium ion concentration, an osmotic pressure, or an antibody concentration, and
wherein in a case where a plurality of pieces of the temporary culture condition data are acquired by the second acquisition unit, the first derivation unit derives the predicted culture result data for each of the plurality of pieces of the temporary culture condition data, and selects the best temporary culture condition data having the best predicted culture result data among the plurality of pieces of the temporary culture condition data, and
the culture conditions in the production culture process are set according to the best temporary culture condition data.

2. The non-transitory computer-readable storage medium according to claim 1, the program causing the computer to function as:
a first output control unit that performs a control for outputting the predicted culture result data.

3. The non-transitory computer-readable storage medium according to claim 1, the program causing the computer to function as:
a second output control unit that performs a control for outputting the best temporary culture condition data.

4. The non-transitory computer-readable storage medium according to claim 1, the program causing the computer to function as:
a third acquisition unit that acquires the initial record data for learning and the production record data for learning; and
a second derivation unit that derives the learned model by performing the machine learning on the basis of the initial record data for learning and the production record data for learning acquired in the third acquisition unit.

5. A cell culture support apparatus for supporting cell culture from an initial culture process, wherein cells into which an antibody gene has been introduced for a production of an antibody-based medicine is cultured using a culture medium, to a production culture process, wherein the cells are cultured using the culture medium, performed in a facility larger than the initial culture process, the apparatus comprising:
a processor configured to function as:
a first acquisition unit that acquires a learned model indicating a relationship between the initial culture process and the production culture process, derived by performing machine learning on the basis of initial record data for learning including a set of culture condition data indicating a record of culture conditions in the initial culture process and culture result data indicating a record of culture results at the end of the initial culture process, and production record data for learning, corresponding to the initial record data for learning and including a set of culture condition data indicating a record of culture conditions in the production culture process and culture result data indicating a record of culture results at the end of the production culture process;
a second acquisition unit that acquires initial record data for analysis including a set of the culture condition data indicating the record of the culture conditions and the culture result data indicating the record of the culture results in the initial culture process, and temporary culture condition data indicating temporary culture conditions in the production culture process; and
a first derivation unit that derives predicted culture result data obtained by predicting the culture result data in the production culture process, from the learned model acquired in the first acquisition unit, and the initial record data for analysis and the temporary culture condition data acquired in the second acquisition unit,
wherein the learned model is acquired by performing machine learning using the culture result data of the production culture process as an objective variable and using the initial record data for learning and the culture condition data of the production culture process as explanatory variables,
the predicted culture result data, which is the target variable output by the learned model, is derived by inputting initial record data for analysis and the temporary culture condition as the explanatory variables into the learned model, and the culture result data and the predicted culture result data include any one of a cell viability, the number of cells, the number of viable cells, a cell diameter, a hydrogen ion index, an oxygen concentration, a carbon dioxide concentration, a glutamate concentration, a lactose concentration, an ammonium concentration, a sodium ion concentration, a potassium ion concentration, an osmotic pressure, or an antibody concentration, and
wherein in a case where a plurality of pieces of the temporary culture condition data are acquired by the second acquisition unit, the first derivation unit derives the predicted culture result data for each of the plurality of pieces of the temporary culture condition data, and selects the best temporary culture condition data having the best predicted culture result data among the plurality of pieces of the temporary culture condition data.

6. A method, performed by a processor configured to perform a first acquisition step, a second acquisition step, and a first derivation step, for operating a cell culture support apparatus for supporting cell culture from an initial culture process, wherein cells into which an antibody gene has been introduced for a production of an antibody-based medicine is cultured using a culture medium, to a production culture process, wherein the cells are cultured using the culture medium, performed in a facility larger than the initial culture process, the method comprising:

- the first acquisition step of acquiring a learned model indicating a relationship between the initial culture process and the production culture process, derived by performing machine learning on the basis of initial record data for learning including a set of culture condition data indicating a record of culture conditions in the initial culture process and culture result data indicating a record of culture results at the end of the initial culture process, and production record data for learning, corresponding to the initial record data for learning and including a set of culture condition data indicating a record of culture conditions in the production culture process and culture result data indicating a record of culture results at the end of the production culture process;
- the second acquisition step of acquiring initial record data for analysis including a set of the culture condition data indicating the record of the culture conditions and the culture result data indicating the record of the culture results in the initial culture process, and temporary culture condition data indicating temporary culture conditions in the production culture process; and
- the first derivation step of deriving predicted culture result data obtained by predicting the culture result data in the production culture process, from the learned model acquired in the first acquisition step, and the initial record data for analysis and the temporary culture condition data acquired in the second acquisition step, wherein the learned model is acquired by performing machine learning using the culture result data of the production culture process as an objective variable and using the initial record data for learning and the culture condition data of the production culture process as explanatory variables, the predicted culture result data, which is the target variable output by the learned model, is derived by inputting initial record data for analysis and the temporary culture condition as the explanatory variables into the learned model, and the culture result data and the predicted culture result data include any one of a cell viability, the number of cells, the number of viable cells, a cell diameter, a hydrogen ion index, an oxygen concentration, a carbon dioxide concentration, a glutamate concentration, a lactose concentration, an ammonium concentration, a sodium ion concentration, a potassium ion concentration, an osmotic pressure, or an antibody concentration, and wherein in a case where a plurality of pieces of the temporary culture condition data are acquired by the second acquisition unit, the first derivation unit derives the predicted culture result data for each of the plurality of pieces of the temporary culture condition data, and selects the best temporary culture condition data having the best predicted culture result data among the plurality of pieces of the temporary culture condition data.

* * * * *